United States Patent
Brisby et al.

(10) Patent No.: US 12,357,187 B2
(45) Date of Patent: Jul. 15, 2025

(54) SYSTEMS AND METHODS FOR ASSESSING A PHYSIOLOGICAL PROPERTY OF A BIOLOGICAL TISSUE BASED ON ITS MICROWAVE TRANSMISSION PROPERTIES

(71) Applicants: Helena Brisby, Kullavik (SE); Paul Meaney, Gothenburg (SE); Tomas Rydholm, Gothenburg (SE); Robin Augustine, Uppsala (SE)

(72) Inventors: Helena Brisby, Kullavik (SE); Paul Meaney, Gothenburg (SE); Tomas Rydholm, Gothenburg (SE); Robin Augustine, Uppsala (SE)

(73) Assignee: PROBINGON AB, Uppsala (SE)

( * ) Notice: Subject to any disclaimer, the term of this patent is extended or adjusted under 35 U.S.C. 154(b) by 860 days.

(21) Appl. No.: 17/059,622

(22) PCT Filed: May 22, 2019

(86) PCT No.: PCT/EP2019/063228
§ 371 (c)(1),
(2) Date: Nov. 30, 2020

(87) PCT Pub. No.: WO2019/228887
PCT Pub. Date: Dec. 5, 2019

(65) Prior Publication Data
US 2021/0259570 A1    Aug. 26, 2021

(30) Foreign Application Priority Data
May 31, 2018    (SE) ..................... 1850654-3

(51) Int. Cl.
*A61B 5/0507* (2021.01)
*A61B 5/00* (2006.01)

(52) U.S. Cl.
CPC ............ *A61B 5/0507* (2013.01); *A61B 5/442* (2013.01); *A61B 5/4509* (2013.01);
(Continued)

(58) Field of Classification Search
CPC ..... A61B 5/0507; A61B 5/4509; A61B 5/442; A61B 5/4514; A61B 5/4519;
(Continued)

(56) References Cited

U.S. PATENT DOCUMENTS

2005/0004457 A1    1/2005   Moilanen et al.
2005/0107718 A1    5/2005   Hashimshony
(Continued)

FOREIGN PATENT DOCUMENTS

GB    2428801 A    2/2007

OTHER PUBLICATIONS

Irastorza, R.M. et al. "Modeling of the dielectric properties of trabecular bone samples at microwave frequency". Medical & Biological Engineering & Computing 52, 439-447 (2014) (Year: 2014).*
(Continued)

*Primary Examiner* — Christopher Koharski
*Assistant Examiner* — Helene Bor
(74) *Attorney, Agent, or Firm* — Cozen O'Connor

(57) ABSTRACT

According to one aspect of the invention, a method for assessing physiological properties of a biological tissue is provided. The method comprising the steps of transmitting from a first coaxial probe, receiving at a second coaxial probe and assessing physiological properties. The transmission from the first probe is a microwave signal. The second coaxial probe receives a microwave signal. The first coaxial probe and the second coaxial probe are arranged in connection with the biological tissue. The physiological properties of the biological tissue between the coaxial probes are
(Continued)

assessed based on the microwave signal transmitted and received across the biological tissue. The invention further relates to a system and a coaxial probe useful in performing such a method.

19 Claims, 7 Drawing Sheets

(52) U.S. Cl.
CPC .......... *A61B 5/4514* (2013.01); *A61B 5/4519* (2013.01); *A61B 5/4523* (2013.01); *A61B 5/4533* (2013.01); *A61B 5/4566* (2013.01); *A61B 2562/0228* (2013.01)

(58) Field of Classification Search
CPC ... A61B 5/4523; A61B 5/4533; A61B 5/4566; A61B 2562/0228
See application file for complete search history.

(56) References Cited

U.S. PATENT DOCUMENTS

| | | | | |
|---|---|---|---|---|
| 2005/0197576 A1* | 9/2005 | Luo | ...................... | A61B 8/0875 600/438 |
| 2006/0122621 A1* | 6/2006 | Truckai | .............. | A61B 17/8822 606/93 |
| 2009/0222221 A1* | 9/2009 | Buyukozturk | ............ | G01S 7/41 702/35 |
| 2009/0322349 A1* | 12/2009 | Hancock | .................. | A61B 5/05 324/642 |
| 2010/0121318 A1* | 5/2010 | Hancock | .............. | A61B 5/0507 342/174 |
| 2011/0077509 A1 | 3/2011 | Leibtritz et al. | | |
| 2013/0225960 A1* | 8/2013 | Porch | ................... | A61B 5/0082 600/430 |
| 2014/0128861 A1* | 5/2014 | Leung | .................... | A61B 18/18 606/33 |
| 2018/0325413 A1* | 11/2018 | Petrovic | .............. | A61B 5/0507 |
| 2019/0388001 A1* | 12/2019 | Leibfritz | .............. | A61B 5/0507 |

OTHER PUBLICATIONS

K. S. Bialkowski et al., "Biomedical imaging system using software defined radio", Proceedings of 2015 IEEE Antennas and Propagation Society International Symposium (APSURSI), pp. 542-543, Jul. 2015 (Year: 2015).*

International Search Report and Written Opinion mailed Feb. 8, 2019; International Patent Application No. PCT/EP2019/063228 filed on May 22, 2019. ISA/EP.

* cited by examiner

Fig 7
A
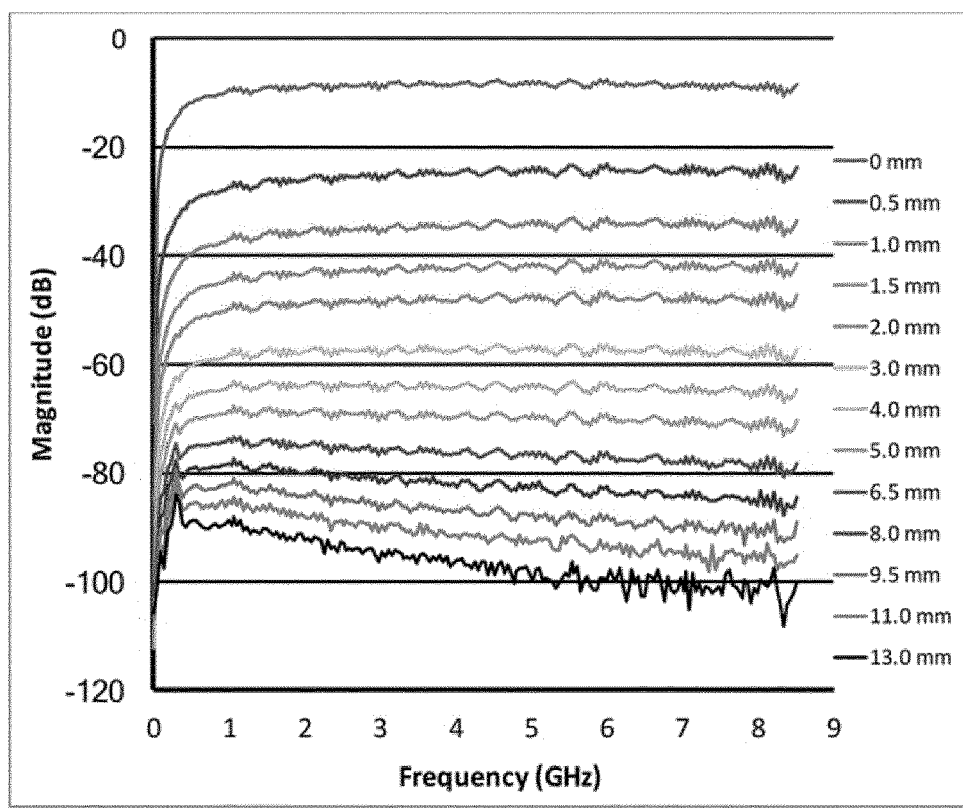
B
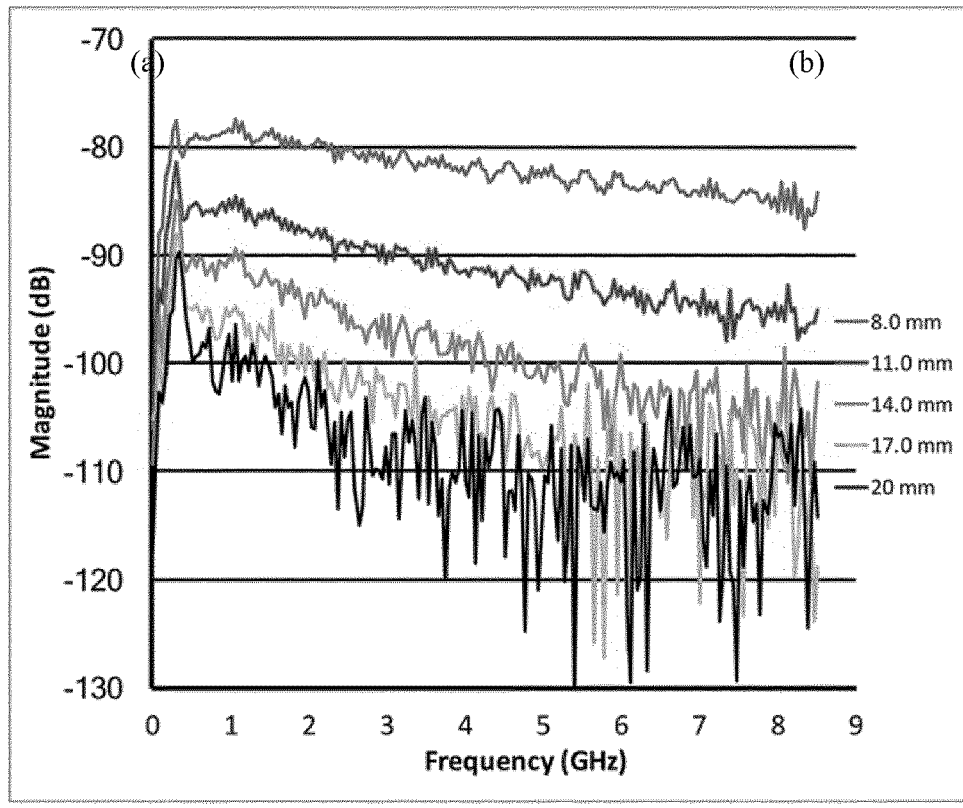

Fig 8
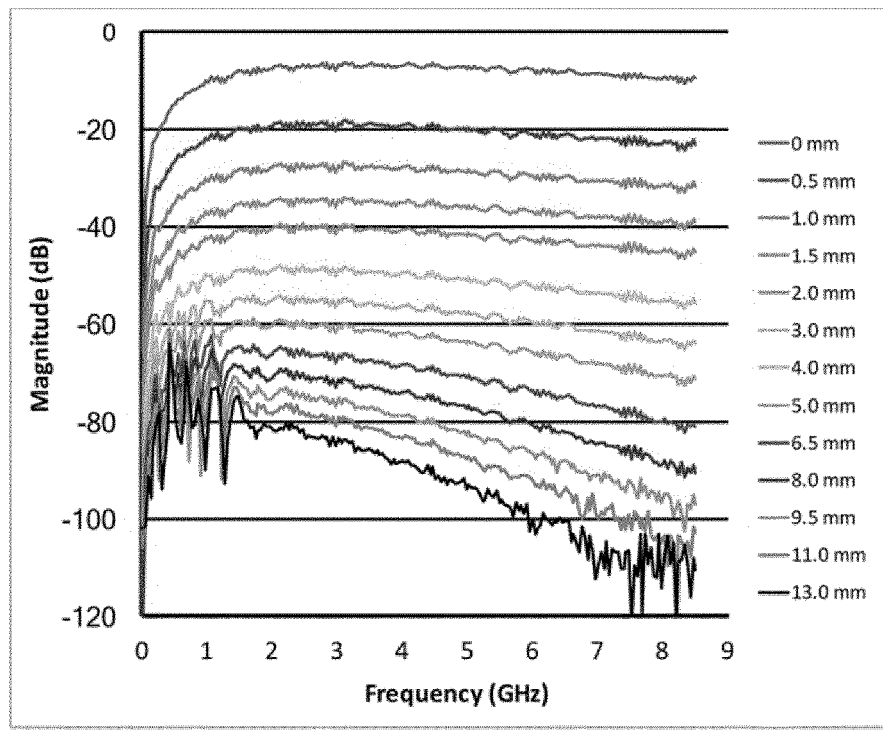
A
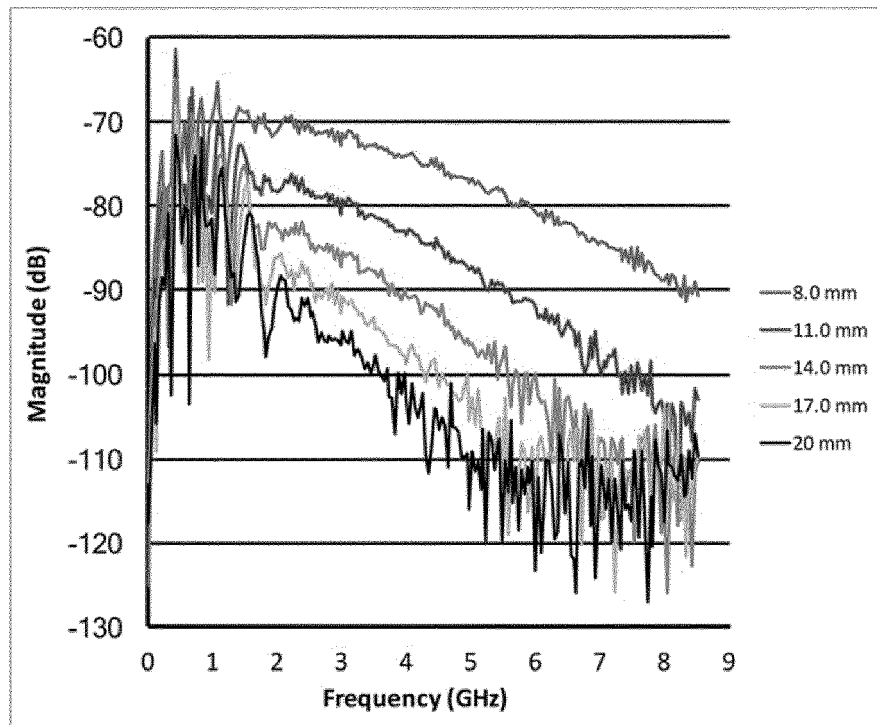
B

SYSTEMS AND METHODS FOR ASSESSING A PHYSIOLOGICAL PROPERTY OF A BIOLOGICAL TISSUE BASED ON ITS MICROWAVE TRANSMISSION PROPERTIES

CROSS-REFERENCE TO RELATED APPLICATION

This application is a 35 U.S.C. § 371 national stage application of PCT Application No. PCT/EP2019/063228 filed on May 22, 2019, entitled "SYSTEMS AND PROCESSES FOR ASSESSING A PHYSIOLOGICAL PROPERTY OF A BIOLOGICAL TISSUE ON THE BASIS OF ITS MICROWAVE TRANSMISSION PROPERTIES," which claims priority to Swedish Patent Application No. 1850654-3 filed on May 31, 2018, each of which are incorporated herein in their entirety by reference.

TECHNICAL FIELD

The present invention generally relates to the field of dielectric probes and more particularly to methods for assessing physiological properties of a biological tissue based on its microwave transmission properties, and associated uses, and dielectric probes useful in such methods.

BACKGROUND ART

Measured properties of biological tissue convey important information for researchers and health care workers and play a vital role in medical treatment decisions. However, there are a number of problems associated with measurements, some stemming from the fact that it is usually undesirable or even impossible to remove the biological tissue, and that taking measurements is also associated with pain and inconvenience to the patient. Therefore there is a need for improved devices and methods which provide measurements in situ.

For example, back and neck pain is a large contributor to missed working days and is a general nuisance for the population. It is in fact reported to be the leading cause of disability worldwide.

In connection with back and neck pain but also for other reasons, part of the population requires some form of intervention which often involves the fusion of two or more vertebrae. This can be achieved via a surgical procedure whereby hardware is used to fix and stabilize the vertebrae until a complete and solid fusion is confirmed. This hardware commonly involves posterior pedicle screws inserted into the vertebrae to be fused, which screws are connected external to the vertebrae through rods spanning several continuous vertebrae to supply sufficient support during fixation.

In some cases, it is uncertain whether the vertebrae will be strong enough to withstand the mechanical pressure on the pedicle screws. Dual-energy x-ray absorptiometry (DXA) can sometimes be inconclusive in these situations due to artefacts from overlying tissues and the fact that there can be considerable variation in density between vertebrae. An improved device and method for indicating sufficiently strong versus insufficiently strong vertebrae for fusion surgery is desired.

Even where it is possible to remove biological tissue for measurement, this can involve invasive procedures introducing not only risk for the patient but also requiring use of sterile equipment, adherence to proper procedures and access to laboratory equipment, some or all of which may be impossible or unavailable at remote or economically deprived locations. This is thus a further driver of the need for affordable and robust devices and methods for measuring properties of biological tissue in situ.

SUMMARY OF THE INVENTION

The present invention aims to provide an easy to handle, cheap and robust microwave based apparatus for assessing and/or measuring properties of biological tissue in situ, as well as corresponding methods for assessing and/or measuring properties of biological tissue in situ.

While existing methods, such as reflection-based microwave coaxial probes or dual-energy x-ray absorptiometry (DXA), may provide some information about the biological tissue, they have a number of drawbacks. For example reflection-based microwave coaxial probes are prone to errors from poor tissue contact, in addition the penetration depth of such measurements is typically on the order of 0.25 mm, thereby lacking in providing a reliable indicator of the biological tissue over a more meaningful depth without multiple measurements.

For another example, a DXA scan is performed over a larger area—typically examining multiple vertebrae—and thereby results in an average value, masking any local variations. In addition, any x-ray based scan may include artefacts induced by different calcifications or other tissue variation in overlying or surrounding tissue.

The inventors of the present invention have identified a need for improvements in providing devices and methods for assessing and/or measuring properties of a biological tissue and associated uses that are designed to overcome or at least mitigate the problems stated above, and which provide improved functionality in a more robust realisation with reliable benefits.

The present invention thus provides a concept based on measuring and analysing the transmission of microwaves in biological tissue by an arrangement with coaxial probes, resulting in an improved assessment and/or determination of properties of the biological tissue. This concept is useful in a variety of applications as detailed below.

The properties that are assessed are physiological properties. Physiological properties can relate to the composition of the biological tissue, such as water content, fat or lipid content, or protein content; density, texture, strength, and the like.

The properties that are measured are dielectric properties, such as dielectric constant, relative permittivity, and conductivity.

An object of the present invention is to provide a device for assessing physiological dielectric properties of a biological tissue which overcomes the problems stated above.

A further object of the present invention is to provide a system for assessing physiological properties of a biological tissue which overcomes the problems stated above.

A further object of the present invention is to provide a method for assessing physiological properties of a biological tissue with advantages relating to reliability, security and/or flexibility.

A further object of the present invention is to provide a device for measuring dielectric properties of a biological tissue which overcomes the problems stated above.

A further object of the present invention is to provide a method for measuring dielectric properties of a biological tissue which overcomes the problems stated above.

A further object of the present invention is to provide a method for measuring dielectric properties of a biological tissue with advantages relating to reliability, security and/or flexibility.

The present invention is defined according to the independent claims. Preferred embodiments are set forth in the dependent claims.

Thus, in a first aspect the invention relates to a method for assessing at least one physiological property of a biological tissue, the method comprising the steps of:
- transmitting a microwave signal from a first coaxial probe;
- receiving a microwave signal at a second coaxial probe;
- wherein the first coaxial probe and the second coaxial probe are arranged in connection with the biological tissue; and
- assessing the at least one physiological property of the biological tissue based on measures of the microwave signal transmitted and received across the biological tissue between the coaxial probes.

In one embodiment, the assessment of the at least one physiological property of the biological tissue is based on the measured amplitudes and phases of the microwave signal transmitted and received across the biological tissue between the coaxial probes.

In one embodiment, the first coaxial probe and the second coaxial probe are arranged on opposite sides of the biological tissue and the end surface of the first coaxial probe and the end surface of the second coaxial probes are arranged to be parallel, or at an angle of less than 90°, and opposing each other. Said angle may be less than 90°, less than 75°, less than 60°, less than 45°, less than 30° or less than 15°.

In one embodiment, the first coaxial probe and the second coaxial probe are arranged on the same side of the biological tissue and the first and second coaxial probes are arranged to be parallel, or at an angle of no more than 90°. Said angle may be no more than 90°, no more than 75°, no more than 60°, no more than 45°, no more than 30° or no more than 15°.

In one embodiment, the biological tissue is bone tissue, skin tissue, connective tissue, tendons, cartilage, muscle, adipose tissue, fibrous tissue, or organ tissue.

In one embodiment, the biological tissue is bone tissue and the first coaxial probe is inserted in a first pedicle canal in a vertebrae and a second coaxial probe is inserted in a second pedicle canal in a vertebrae.

In one embodiment, the end surface of the first coaxial probe is arranged at a distance of 5 mm to 5 cm from the end surface of the second coaxial probe.

In one embodiment, the microwave signal is transmitted using a software defined radio.

In one embodiment, the microwave signal has a frequency greater than 2 GHz and less than 10 GHz.

In one embodiment, the assessment of the physiological property is based on a calculation of a dielectric property of the biological tissue based on the microwave signal transmitted and received across the biological tissue between the coaxial probes.

In one embodiment, the at least one dielectric property is selected from the group consisting of dielectric constant, relative permittivity, and conductivity.

In one embodiment, the biological tissue is bone tissue and the physiological property is selected from bone density and bone strength.

In one embodiment, the first coaxial probe and the second coaxial probe are independently arranged in contact with the biological tissue or at a distance of 5 mm or less from the biological tissue.

In a further aspect, the invention relates to a system for assessing at least one physiological property of a biological tissue, the system comprising:
- a first coaxial probe arranged to be located in connection with the biological tissue and to transmit a microwave signal;
- a second coaxial probe arranged to be located in connection with the biological tissue and to receive a microwave signal;
- a calculation unit in connection with the first coaxial probe and the second coaxial probe, the calculation unit being configured to:
- calculate an assessment of the at least one physiological property of the biological tissue based on the microwave signal transmitted and received across the biological tissue between the coaxial probes.

In one embodiment, the end surface of the first coaxial probe and the end surface of the second coaxial probe are arranged to be opposing each other and parallel, or at an angle of less than 90°, with each other. Said angle may be less than 90°, less than 75°, less than 60°, less than 45°, less than 30° or less than 15°.

In one embodiment, the first coaxial probe and the second coaxial probe are arranged on a pincer or caliper.

In one embodiment, the end surface of the first coaxial probe and the end surface of the second coaxial probe are arranged to be parallel and arranged side-by-side.

In one embodiment, the calculation unit is configured to calculate at least one dielectric property of the biological tissue based on the microwave signal transmitted and received across the biological tissue between the coaxial probes and to calculate an assessment of the at least one physiological property of the biological tissue based on said calculated dielectric property.

In a further aspect, the invention relates to a coaxial probe comprising a central conductor and a second conductor arranged to at least partly surround the central conductor and to be grounded, wherein a tip of the coaxial probe is bent such that the tip is at an angle in comparison with the main part of the coaxial probe; or wherein a tip of the coaxial probe is bevelled such that the surface at the tip of the probe is at an angle in comparison with the main part of the probe; or wherein a tip of the coaxial probe is at an angle to the rest of the probe such that the tip surface of the probe is at an angle in comparison with the main part of that probe, wherein said angle may be 30, 45, 60, 90, 120, 135, 150 degrees or therebetween.

BRIEF DESCRIPTION OF THE DRAWINGS

The invention is described in the following illustrative and non-limiting detailed description of exemplary embodiments, with reference to the appended drawings, wherein:

FIGS. 7A and /B show plots of the $S_{21}$ amplitudes as a function of frequency for multiple separations for a 80:20 glycerin:water bath.

FIGS. 8A and 8B show plots of the $S_{21}$ amplitudes as a function of frequency for multiple separations for the 20:80 glycerin:water bath.

Figure 1:
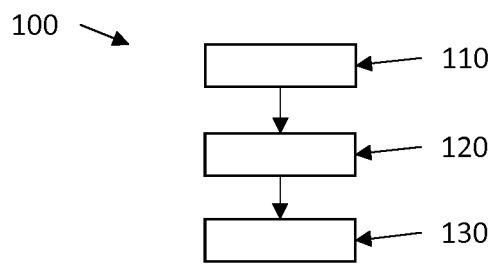
FIG. 1 is a schematic illustration of a method according to a first aspect of the present invention.

All figures are schematic, not necessarily to scale, and generally only show parts necessary in order to elucidate the invention, wherein other parts may be omitted or merely suggested. Throughout the figures the same reference signs designate the same, or essentially the same features.

DETAILED DESCRIPTION

The invention is based on an insight that due to their short penetration depth and large range of errors, current reflection based microwave coaxial probe measurements are ill-suited for measuring dielectric properties of a biological tissue or for assessing physiological properties thereof.

Reflection based measurements are particularly problematic for measuring heterogeneous tissues. The top tissue layer may not be representative of the entire measured biological tissue. For example the steepest temperature gradients may be found at the surface of newly excised tissue. Dielectric properties of biological tissues are very sensitive to temperature variations. Additionally, very often newly excised tissue is covered with a thin layer of blood that can either be fresh or dried depending on the technician and the tissue preparation processes used. With shallow sensing depth blood properties can confound the measured properties of the tissue. These factors and others can easily impact the result when using reflection based measurements. By utilizing a transmission based measurement according to an embodiment of the invention, the penetration depth is increased and provides improved measurements for heterogeneous tissues.

According to one aspect of the invention, a method for assessing at least one physiological property of a biological tissue is provided. The method comprises the steps of transmitting from a first coaxial probe, receiving at a second coaxial probe and assessing the at least one physiological property of the biological tissue. The transmission from the first probe is a microwave signal. The second coaxial probe receives a microwave signal. The first coaxial probe and the second coaxial probe are arranged in connection with the biological tissue. The at least one physiological property of the biological tissue between the coaxial probes is assessed based on measures of the microwave signal transmitted and received across the biological tissue.

In one embodiment, the physiological property is assessed based on examination of the measured amplitude and/or phase of the transmitted microwave signal. The measured amplitude and/or phase of the microwave signal transmitted through a biological tissue test sample with unknown properties can be correlated with measured amplitude and/or phase of microwave signal transmitted through biological tissue control or standard samples with known physiological properties to create a "look-up table" for the type of tissue that is to be examined and assessed.

In one embodiment, the physiological property is assessed based on a calculation of the dielectric properties of the biological tissue, which dielectric properties are calculated based on the transmitted microwave signal as detailed below. The physiological property can then be assessed based on algorithms correlating dielectric properties with physiological properties, or by correlating the dielectric properties of the biological tissue test sample with unknown properties with the dielectric properties of the biological tissue control or standard samples with known dielectric properties to create a "look-up table" for the type of tissue that is to be examined and assessed. Physiological properties can relate to the composition of the biological tissue, such as water content, fat or lipid content, protein content, mineralization or calcification; density, texture, strength, and the like.

By utilizing a transmission based measurement according to an embodiment of the invention, the penetration depth of the measurement would be the distance between the first and second coaxial probes. In this context, the distance between the first and second coaxial probe is the distance between the first coaxial probes position which is in connection with the measured biological tissue and the second coaxial probes position which is in connection with the measured biological tissue. By using two probes and transmitting a signal from one to the other the signal interrogates the whole volume and is more representative of the biological tissue compared to the reflection based probe approach. In addition, the transmission type measurement is less vulnerable to poor contact with the biological tissue and cable bending, in comparison to the reflective type measurement.

Further, the ability to perform direct measurements of biological tissue during surgery could assist in decision making and thereby minimize the number of repeated surgeries and/or inappropriate treatments, reducing health care costs while improving overall patient quality of life. In cases where the measurements are outside of a predefined span or similar, the original medical treatment plan can be aborted and instead alternative surgical strategies can be used to improve the probability of success.

Further still, by utilizing coaxial probes, a number of factors which affect methods using x-ray, in particular DXA, are avoided. These may include artefacts from different calcifications in some of the overlying or surrounding tissue such as the aorta and pancreas. By utilizing coaxial probes the actual tissue can be measured directly.

Even more, by utilizing transmission mode measurements with coaxial probes the measurements are less sensitive to the characteristics of the probe contact with the biological tissue. Additionally, the transmission based approach provides an improved stability even with respect to cable bending.

In one embodiment, the first coaxial probe and/or the second coaxial probe are arranged in contact with the biological tissue.

The term "contact" in this context means that there is no distance between the first coaxial probe and/or the second coaxial probe and the biological tissue.

In one embodiment, the first coaxial probe and/or the second coaxial probe are arranged in close contact with the biological tissue.

The term "close contact" in this context means that there is a distance between at least one of the first and second coaxial probes and the biological tissue, the distance being less than approximately 1 mm, a distance below 0.5 mm, below 0.2 mm or similar.

The term "connection" in this context may for example include that an additional tissue layer is present between the measured tissue and the first coaxial probe and/or the second coaxial probe.

A method according to the present invention overcomes the problems stated previously.

In one embodiment, the coaxial probe may comprise a first and a second conductor. The first conductor may be a central conductor and arranged to transmit a signal. The second conductor may be arranged to at least partly surround the first/central conductor and to be grounded.

The coaxial probes used according to the invention are preferably of medical grade, that is they are capable of being safely inserted into a human or animal body during surgical procedure. Notably, the coaxial probes are preferably capable of withstanding sterilisation procedures, such as by autoclaving or γ-irradiation.

In one embodiment, the tip of the coaxial probe may be spring loaded.

In one embodiment, the coaxial probe may comprise a flexible wire, a connector and a tip.

In one embodiment, the first conductor and/or the second conductor of the coaxial probe may be spring loaded.

In one embodiment, the first coaxial probe, the second coaxial probe and/or the calculation unit may comprise a rectifier. By this, radio frequency signals may be converted to direct current signals.

In one embodiment, the received microwave signal may be amplified.

In one embodiment, the received microwave signal may be amplified in an amplifier unit.

In one embodiment, the second coaxial probe may comprise an amplifier unit.

In one embodiment, the assessment of the at least one physiological property of the biological tissue is based on the measured amplitudes and phases of the microwave signal transmitted and received across the biological tissue between the coaxial probes.

In one embodiment, the first coaxial probe and the second coaxial probe are arranged on opposite sides of the biological tissue and the end surface of the first coaxial probe and the end surface of the second coaxial probes are arranged to be parallel, or at an angle of less than 90°, and opposing each other. Said angle may be less than 90°, less than 75°, less than 60°, less than 45°, less than 30° or less than 15°.

Directing either one or both of the first and the second coaxial probes in the direction of the other one of the first and the second coaxial probes may be used to increase the strength of the transmitted microwave signal. By this, the measurement depth in the measured tissue may be increased. By this, the microwave signal transmitted from the first coaxial probe may be directed so that the signals general direction of propagation is towards the receiving second coaxial probe.

In one embodiment, the first coaxial probe and the second coaxial probe are arranged on the same side of the biological tissue and the first and second coaxial probes are arranged side-by-side.

In one embodiment, the first coaxial probe and the second coaxial probe are arranged on the same side of the biological tissue and the first and second coaxial probes are arranged to be parallel, or at an angle of no more than 90°, and arranged side-by-side. Said angle may be no more than 90°, no more than 75°, no more than 60°, no more than 45°, no more than 30° or no more than 15°.

By this, both the first coaxial probe and the second coaxial probe is arranged on the same side of a biological tissue, hence access to only one side of the biological tissue is necessary. Thus the handling is improved.

By positioning either one or both of the first and the second coaxial probes in an orientation other than being aimed directly at the other one of the first and the second coaxial probes, the strength of the transmitted microwave signal may be decreased and the relative strength of a scattered microwave signal may be increased. The scattered microwave signal comprises an indication of physiological and/or dielectric properties of the biological tissue extending outside the line between the coaxial probes. The scattered signal is calculated based on the microwave signal transmitted, scattered and received across the biological tissue.

In one embodiment, a scattered microwave signal may be used to assess the physiological properties and/or calculate dielectric properties of a region of biological tissue beyond the tissue which the first coaxial probe and the second coaxial probe are arranged in connection with. In one alternative, the end surfaces of the first and second coaxial probes are arranged in contact with the same side surface of the biological tissue, e.g. for a tissue having an anterior and a posterior portion both the first and second coaxial probes contact the anterior portion.

By detecting a scattered signal, physiological and/or dielectric properties of the biological tissue extending beyond an axis extending between the coaxial probes can be assessed/calculated. In this way physiological and/or dielectric properties of adjacent biological tissue may be assessed/calculated. The adjacent biological tissue is the tissue beyond the tissue in connection with the first coaxial probe and the second coaxial probe.

In one embodiment, the biological tissue may be bone tissue, skin tissue, connective tissue, tendons, cartilage, muscle, adipose tissue, fibrous tissue, or organ tissue.

The overall success rate in spinal fusion surgery is lower than average when performed on bone with low density and strength, and failed fixation can lead to significant patient inconvenience and risk, not to mention increased costs due to repeated treatments, including multiple surgeries. There is thus a need to perform an easy and adequate assessment of the properties of bone tissue for spinal fusion surgery.

Performing direct measurement of the bone tissue during surgery could assist in the decision making and thereby minimize the number of repeated surgeries and/or inappropriate treatments, reducing health care costs while improving overall patient quality of life. In cases where the method determines that the bone tissue lacks sufficient density and/or is too weak, alternative surgical strategies can be used to improve the probability of success.

Further, by utilizing coaxial probes, a number of additional factors which affect x-ray methods are avoided. By utilizing coaxial probes properties of the actual bone tissue can be measured.

In one embodiment, the biological tissue may be skin tissue.

By performing direct transmission mode measures of the skin tissue an improved detection accuracy of conditions affecting dielectric properties of the skin tissue is achieved. In one embodiment, values of dielectric properties can be used to assess the status of the skin tissue as being affected or not affected by the condition in question.

As a non-limiting example, an improved method of finding skin tissue or assessing skin tissue possibly affected by post-kala-azar dermal leishmaniasis (PKDL) or cancer is achieved. In one embodiment, the method may be used for finding the edges of a biological tissue having a volume affected by a condition affecting the dielectric properties. By this, a surgeon can more accurately remove affected tissue without leaving residual affected tissue, yet conserving unaffected tissue at site.

In one embodiment, wherein the biological tissue is bone tissue, the first coaxial probe may be inserted in a first pedicle canal in a vertebrae and the second coaxial probe may be inserted in a second pedicle canal in the vertebrae. In an alternative embodiment wherein the tissue is bone tissue, the first coaxial probe has been inserted in a first pedicle canal in a vertebrae and the second coaxial probe has been inserted in a second pedicle canal in the vertebrae.

Performing direct measurement of the bone tissue during surgery could assist in the decision making and thereby minimize the number of repeated surgeries, reducing health care costs while improving overall patient quality of life. In cases where the method determined that the vertebrae are weak, alternative surgical strategies can be used to improve the probability of success.

Further, by utilizing coaxial probes, a number of additional factors which affects x-ray methods are avoided. For x-ray scans of the spine, the rib cage makes measurement almost impossible. By utilizing coaxial probes the actual bone tissue at the correct position of the vertebrae may be measured.

In one embodiment, the end surface of the first coaxial probe may be arranged at a distance of 0.5 cm to 5 cm from the end surface of the second coaxial probe.

In one embodiment, the end surface of the first coaxial probe may be arranged at a distance of 1 cm to 5 cm from the end surface of the second coaxial probe.

In one embodiment, the end surface of the first coaxial probe may be arranged at a distance of 0.5 cm to 3 cm from the end surface of the second coaxial probe.

In one embodiment, the end surface of the first coaxial probe may be arranged at a distance of 1 cm to 3 cm from the end surface of the second coaxial probe.

In one embodiment, the end surface of the first coaxial probe may be arranged at a distance of 1 cm to 2 cm from the end surface of the second coaxial probe.

In one embodiment, the microwave signal may be transmitted using a software defined radio.

In one embodiment, the microwave signal may be received using a software defined radio.

By the use of a software defined radio (SDR), a more compact and less expensive realisation of a high dynamic range measurement apparatus may be created. In addition, by using SDR the operational frequency span may be increased, thereby improving measurement.

In one embodiment, the microwave signal may be transmitted using a signal generator.

For example, the signal generator may be a part of a network analyser, a vector network analyser, a stand alone unit and/or a combination thereof. The signal generator may be in communication with a receiving unit.

The signal generator may generate one, two or more signals from one, two or more signal generators. By generating multiple signals, mixer test and/or measurements may be improved.

In one embodiment, the microwave signal may be transmitted using a vector network analyser.

In one embodiment, the microwave signal may be received using a vector network analyser.

This makes possible the use of some conventional receiving units.

In one embodiment, the microwave signal may have a frequency that is greater than 2 GHz and less than 10 GHz.

In one embodiment, the microwave signal may have a frequency less than 8 GHz.

In one embodiment, the microwave signal may have a frequency less than 6 GHz.

In one embodiment, the microwave signal may have a frequency less than 4 GHz.

In one embodiment, the microwave signal may have a frequency greater than 4 GHz.

In one embodiment, the microwave signal may have a frequency greater than 6 GHz.

In one embodiment, the microwave signal may have a frequency greater than 8 GHz.

By this, the contribution from multi-path signals may be reduced.

In one embodiment, the assessment of the physiological property is based on a calculation of a dielectric property of the biological tissue based on the microwave signal transmitted and received across the biological tissue between the coaxial probes.

By this, a method and system for measuring at least one dielectric property of a biological tissue may be established.

In one embodiment, a plurality of dielectric properties of the biological tissue may be calculated based on the microwave signal transmitted and received across the biological tissue between the coaxial probes.

In one embodiment, the calculation may be performed at a receiving unit.

In one embodiment, the unit receiving the microwave signal may further comprise a calculation unit which is arranged to perform the calculation.

In one embodiment, the received microwave signal may be sent to a central unit, where the central unit may perform the calculation.

In one embodiment, the received microwave signal may be sent to a calculation unit, where the calculation unit may perform the calculation.

In one embodiment, the calculation may be based on the transmitted microwave signal. For example, a signal generator may generate a signal for the transmitting probe and provide information relating to the signal to provide a reference signal.

In one embodiment, the calculation of the at least one dielectric property of the biological tissue may be based on the amplitudes and phases of the microwave signal transmitted and received across the biological tissue between the coaxial probes.

In one embodiment, the calculation unit may comprise an amplifier unit arranged to amplify the signal from the second coaxial probe.

In one embodiment, the received microwave signal may be amplified by an amplifier unit arranged between the second coaxial probe and the calculation unit.

An exemplary amplifier module may incorporate a single-pole/single-throw (SPST) switch, a single-pole/double-throw (SPDT) switch and a low noise amplifier (LNA).

In one embodiment, the at least one dielectric property may comprise a dielectric constant.

In one embodiment, the dielectric properties may comprise a dielectric constant.

In one embodiment, the method may further comprise correlating the at least one measured dielectric properties of the biological tissue with at least one physiological property of said tissue.

In one embodiment, the method may further comprise correlating the measured dielectric properties of the biological tissue with a physiological property of said tissue.

In one embodiment, the biological tissue may be bone tissue and the physiological property may be selected from bone density and bone strength.

For example, the dielectric properties of the trabecular bone are directly related to the bone density, which is correlated to bone strength.

By this, it is possible to predict success of a fixation with posterior pedicle screws connected by rods in several continuous vertebrae to provide hardware fixation with the intention to stabilize the vertebrae.

By utilizing coaxial probes and the improved method according to this or the method described in any embodiment, measurements of the vertebrae suitability on each bone, and/or bone position, directly during the surgical session at least an individually designed surgery plan and improved reliability may be achieved.

In one embodiment, the bone tissue may be augmented with bio-compatible cements to strengthen the bone tissue where the pedicle screws are connected. There is however a small risk of a piece of cement breaking off and entering the blood stream and eventually causing harm. By utilizing coaxial probes and the improved method, the use of bio-compatible cements may be reduced.

In one embodiment, screws extending in, over or through more than one segment of bone tissue may be used. These multi-bone screws require a more invasive surgery. By utilizing coaxial probes and the improved method, the use of multi-bone screws may be reduced.

In one embodiment, the method may further comprise calculating the distance between the first coaxial probe and the second coaxial probe.

In one embodiment, the physiological properties of the biological tissue between the coaxial probes are assessed based on the microwave signal transmitted and received across the biological tissue, and on the distance between the first coaxial probe and the second coaxial probe.

In one embodiment, the dielectric properties of the biological tissue between the coaxial probes are calculated based on the microwave signal transmitted and received across the biological tissue, and on the distance between the first coaxial probe and the second coaxial probe.

In one embodiment, the method according to the invention provides an assessment of at least one property of a biological tissue, wherein the assessment is useful to a medical practitioner to determine a diagnosis relative the biological tissue and the patient.

In one embodiment the method does not include an intellectual step of deducing a diagnosis based on the assessment of the at least one property of the biological tissue.

In one embodiment, wherein the biological tissue is accessible by performing a surgical step to introduce a probe in a human or animal body, such surgical steps are, as such, not part of the method according to the invention.

In a further aspect, the invention relates to a system for assessing at least one physiological property of a biological tissue. The system comprises a first coaxial probe, a second coaxial probe and a calculation unit. The first coaxial probe is arranged to be located in connection with the biological tissue and to transmit a microwave signal. The second coaxial probe is arranged to be located in connection with the biological tissue and to receive a microwave signal. The calculation unit is in connection with the first coaxial probe and the second coaxial probe. The calculation unit is configured to calculate an assessment of the at least one physiological property of the biological tissue based on the microwave signal transmitted and received across the biological tissue between the coaxial probes.

In one embodiment, the end surfaces of the first and second coaxial probes may be arranged to be opposing each other and parallel, or at an angle of less than 90°, with each other. Said angle may be less than 90°, less than 75°, less than 60°, less than 45°, less than 30° or less than 15°.

In one embodiment, the end surfaces of the first and second coaxial probes may be arranged to be at an angle with each other. The first and second coaxial probes may for example be pointing at a mutual point in space and/or be arranged to have a specific angle towards the biological tissue. For example being perpendicular to the surface of the biological tissue to be measured. Another example of angular arrangement may be to coincide with a recess, a hole and/or canal produced by a surgeon in the biological tissue.

In one embodiment, a tip of the first coaxial probe and/or a tip of the second coaxial probe may be bent such that the tip of the first coaxial probe and/or the tip of the second coaxial probe is at an angle in comparison with the main part of the first coaxial probe and/or the second coaxial probe, respectively. By this, the direction of the propagation and/or receiving of the microwave signal may be optimized. For example the probes may be inserted in a first and second direction and still have the tips facing each other. This may provide a stronger signal when the first and second coaxial probes are arranged at an angle with each other, for example when inserted in pedicle arms in a vertebrae.

In one embodiment, a tip of the first and/or second coaxial probe may be bevelled such that the surface at the tip of the probe is at an angle in comparison with the main part of that probe.

By this, the direction of the propagation and/or receiving of the microwave signal may be optimized. For example the probes may be inserted in a first and second direction and still have the tips facing each other. This may provide a stronger signal when the first and second coaxial probes are arranged at an angle with each other, for example when inserted in pedicle arms in a vertebrae.

In one embodiment, a tip of the first and/or second coaxial probe may be coplanar. This makes possible improvements in identification and management of a volume affected by a condition affecting the dielectric properties of a biological tissue.

In one embodiment, a tip surface of the first and/or second coaxial probe may be at an angle to the rest of the probe such that the tip surface of the probe is at an angle in comparison with the main part of that probe. This angle may as a non-limiting example be 30, 45, 60, 90, 120, 135, 150 degrees or therebetween.

By this, the direction of the propagation and/or receiving of the microwave signal may be optimized. For example the probes may be inserted in a first and second direction and still have the tip surface facing each other. This may provide a stronger signal when the first and second coaxial probes are arranged at an angle with each other, for example when inserted in pedicle arms in a vertebrae.

In one embodiment, the first coaxial probe and/or the second coaxial probe may comprise a handle. The handle may be arranged to indicate a rotational direction. The indication may correspond with the direction of a bent tip, a coplanar tip, and/or the direction in which the tip is bevelled.

In one embodiment, the first and second coaxial probes are arranged on a pincer or caliper. This allows a user to easily position the probes on opposite sides of the tissue and simultaneously measure the distance between the probes.

In one embodiment, the end surfaces of the first and second coaxial probes may be arranged to be parallel, or at an angle of no more than 90°, and arranged side-by-side. Said angle may be no more than 90°, no more than 75°, no more than 60°, no more than 45°, no more than 30° or no more than 15°.

In one embodiment, at least one of the coaxial probes may for example be a semi-rigid coaxial cable.

In one embodiment, at least one of the coaxial probes may be an open ended coaxial probe.

This allows low cost manufacture of the coaxial probe. Further savings may be achieved by utilizing a low cost disposable coaxial probe, removing the requirement for on-site sterilization.

In one embodiment, the coaxial probes may for example be manufactured using micro fabrication techniques.

By this, the coaxial probe will be small enough to fit inside a canal of limited width, such as one produced by a surgeon using existing pedicle probes or similar.

In one embodiment, at least one of the coaxial probes may have a tip that has a diameter in the range 1.2-3.6 mm. In some embodiments, the face of the probe is cut at an angle relative the axis of the coaxial probe. In such embodiments the probe opening will have an oval shape with a major radius that is longer than the diameter of the tip.

By this, the coaxial probe will be easy to arrange into contact with the biological tissue or bone tissue. By the use of transmission mode measurements a thin tip is viable without losing penetration depth, thereby enabling a more precise measurement.

In one embodiment, the calculation unit is configured to calculate at least one dielectric property of the biological tissue based on the microwave signal transmitted and received across the biological tissue between the coaxial probes and to calculate an assessment of the at least one physiological property of the biological tissue based on said calculated dielectric property.

In one embodiment, the biological tissue which the first and the second coaxial probe is arranged to measure may be skin tissue.

By performing direct transmission mode measures of the skin tissue an improved detection accuracy of conditions affecting dielectric properties of the skin tissue is achieved. As a non-limiting example, an improved method of finding skin tissue affected by post-kala-azar dermal leishmaniasis (PKDL) is achieved. As a further example, an improved method of finding skin cancer lesions is achieved.

It is also advantageous, in both the method and the system according to the invention, to determine the distance between the coaxial probes or adapt the system so as to be configured to measure the distance between the open ends of the coaxial probes. This can be done in a number of ways, including the use of pincer or caliper probes as discussed below, or determining the relative positions of two or more points with known positions relative the open ends of the probes to calculate the absolute positions of the open ends of the coaxial probes and thereby obtaining a distance between the open ends.

In one embodiment, the first coaxial probe and the second coaxial probe may be arranged as a pincer or caliper probe.

The term "pincer probe" in this context means a pincer or caliper having at least two parts forming at least one gripping means. At least two of the gripping means are coaxial probes, or at least in that the gripping tip of the pincer probe are coaxial probes. The pincer probe may be arranged so that a biological tissue may be pinched or gripped therein in such a way that the at least two probes contacts the pinched or gripped biological tissue. The pincer probe further comprises means for determining the distance between the coaxial probes, for use in calculation of the dielectric properties of the biological tissue. Such means are well-known in connection with pincers and calipers.

The system may be adapted to carry out any method or combination of methods described in disclosed embodiments.

In a further aspect, the invention relates to coaxial probes as defined above.

In one embodiment, the invention relates to a coaxial probe comprising a central conductor and a second conductor arranged to at least partly surround the central conductor and to be grounded, wherein a tip of the coaxial probe is bent such that the tip is at an angle in comparison with the main part of the coaxial probe.

In one embodiment, the invention relates to a coaxial probe wherein a tip of the coaxial probe is bevelled such that the surface at the tip of the probe is at an angle in comparison with the main part of the probe.

In one embodiment, the invention relates to a coaxial probe wherein a tip of the coaxial probe is at an angle to the rest of the probe such that the tip surface of the probe is at an angle in comparison with the main part of that probe, wherein said angle may be 30, 45, 60, 90, 120, 135, 150 degrees or therebetween.

Obtaining Dielectric Properties

For probes intended to be arranged on opposite sides of a biological tissue, a calibration measurement may be taken with the two probes touching. These measurements include both the magnitude (dB) and phase (radians or degrees) and are acquired over a broad bandwidth. Afterwards, similar measurements are taken with the two probes taken across the desired piece of tissue. It is important to know the physical distance between the probes to calculate the slopes of the magnitudes and the phases. To do this for the phases, the phases need to be "unwrapped." That is, in most measurement systems, the phases are typically reported only between −180 to +180 degrees. When it is like this, there are typically jumps in the phases. Utilizing the data over a broad bandwidth allows one to perform this unwrapping. Unwrapping of measurement phases may be performed as known in the art (e.g. Meaney et al., Med. Phys. 44 (8), August 2017).

For accurately computing the phase slope, it will be important to know whether the correct number of multiples of 360 degrees has been added or subtracted to the measurement phase.

These slopes of the phases and magnitudes are then used as described below to compute the permittivity and conductivity.

In general, the far field signals measured at one antenna due to a signal propagating from another are proportional to $1/r^2$ and $e^{-jkr}$, where r is the separation distance and k is the complex wavenumber. This relationship can be written as:

$$E_{received} = C * \frac{e^{-jkr}}{r^2} = C * \frac{e^{ij\beta r - \alpha r}}{r^2} = \left[c_1 \frac{e^{\alpha r}}{r^2}\right] * \left[c_2 e^{-j\beta r}\right] \quad (1)$$

where C, $c_1$, and $c_2$ are constants, $\beta$ is the phase constant, and $\alpha$ is the attenuation coefficient. In this case, the equation has been separated into the real and imaginary parts, respectively.

From the first of the last two terms, the amplitude (dB) can be written as:

$$\text{Magnitude} = 20*\log_{10}(c_1) - 8.68589\alpha r - 20*\log_{10}(r^2) = c_{1a} - 8.68589\alpha r - 20*\log_{10}(r^2) \quad (2)$$

If we add a factor of $20*\log_{10}(r^2)$ to this equation which is possible since the distance r is known, the resulting equation is:

$$\text{Magnitude} = c_{1a} - 8.68589\alpha r \quad (3)$$

where $c_{1a}$ is a constant and the slope is just $-8.68589\alpha$. Therefore, $\alpha$ can be computed directly from the measurement data as a function of the magnitude slope once the $20*\log_{10}(r^2)$ term has been added.

Similarly, by taking the natural logarithm of the last term in equation 1, we get:

$$\text{Phase} = c_{2a} - \beta r \quad (4)$$

where $c_{2a}$ is a constant and $\beta$ is the phase constant in radians/m. In this case, $\beta$ can be computed directly from the measurement data since it is the phase slope.

Once $\alpha$ and $\beta$ have been determined, the dielectric properties can be solved for directly:

$$\beta - j\alpha = \sqrt{k^2} = \omega^2 \mu_0 \varepsilon_0 \varepsilon_r - j\omega\mu_0 \sigma \quad (5)$$

where $\omega$ is the frequency in radians, $\mu_o$ is the free space magnetic permeability, $\varepsilon_0$ is the free space electrical permittivity, $\varepsilon_r$ is the relative permittivity, and $\sigma$ is the electrical conductivity, respectively.

The dielectric properties of the biological tissue can be correlated with the physiological properties of the tissue by measuring the dielectric properties of control tissues with known physiological properties and establishing a correlation model. That dielectric properties can be correlated with i.a. bone mineralization has been shown, see e.g. Meaney et al., *International Journal of Biomedical Imaging*, 2012, article ID 649612.

The correlation model can be a simple comparison of dielectric properties in healthy and diseased tissues, respectively, or a more advanced classifier such as machine learning algorithms, including support vector machines (SVM).

In one embodiment, the actual raw measurements—e.g. magnitude and phase—may be used to assess the properties of the tissue as the measurements relate to the properties. Calibration measurements with the side-by-side probes may be performed in air, water, and/or a third material or liquid to calibrate the probe. The third material may be biological tissue control or standard samples with known physiological properties. In this way, a "look-up table" for the type of tissue that is to be examined and assessed can be created. The probes may then be placed in connection with the biological tissue under test to assess its properties.

DESCRIPTION IN RELATION TO THE DRAWINGS

The present invention can be used to provide a method or a system for measuring dielectric properties of a biological tissue which overcome or at least mitigate the problems of the prior art and with an improved functionality in a more reliable realisation that provides additional benefits.

The invention is described in the following illustrative and non-limiting detailed description of exemplary embodiments, with reference to the appended drawings, wherein:

FIG. 1 shows a schematic illustration of a method 100 for measuring dielectric properties of a biological tissue, according to an aspect of the present invention. The method comprises transmitting 110 from a first coaxial probe, receiving 120 at a second coaxial probe and calculating 130 the dielectric properties. The transmission 110 from the first coaxial probe is a microwave signal. The second coaxial probe receives 120 a microwave signal. The first coaxial probe and the second coaxial probe are arranged in connection with the biological tissue. The dielectric properties of the biological tissue between the coaxial probes is calculated 130 based on the microwave signal transmitted and received across the biological tissue.

Figure 2:
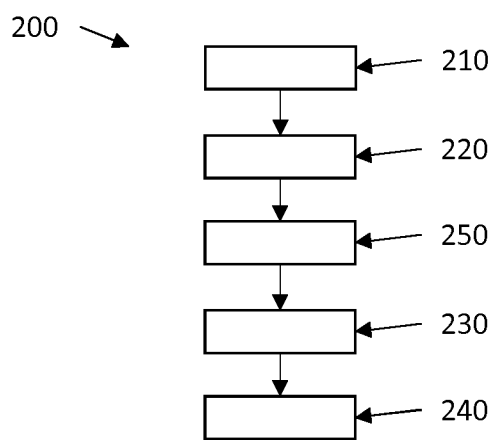
FIG. 2 is a schematic illustration of a method according to one embodiment of the present invention.

FIG. 2 shows a schematic illustration of a method 200 for measuring dielectric properties of a bone tissue, according to an embodiment of the present invention. The method comprises transmitting 210 from a first coaxial probe, receiving 220 at a second coaxial probe, amplifying 250 at an amplification unit, calculating 230 the dielectric properties and correlating 240 the measured dielectric properties of the bone tissue with a physiological property of said tissue. The transmission 210 from the first coaxial probe is a microwave signal, wherein the transmitted microwave signal has a frequency in the span 2 GHz to 10 GHz. The second coaxial probe receives 220 a microwave signal. The first coaxial probe are arranged in connection with the bone tissue in a first pedicle canal in a vertebrae. The second coaxial probe are arranged in connection with the bone tissue in a second pedicle canal in the vertebrae. The received microwave signal from the second coaxial probe is amplified 250 before calculation 230. The dielectric properties of the bone tissue between the coaxial probes is calculated 230 based on the microwave signal transmitted and received across the bone tissue. The dielectric properties that is calculated 230 comprise a dielectric constant. The correlation 240 is between the measured dielectric properties of the bone tissue with the physiological property that is selected from bone density and bone strength.

Figure 3:
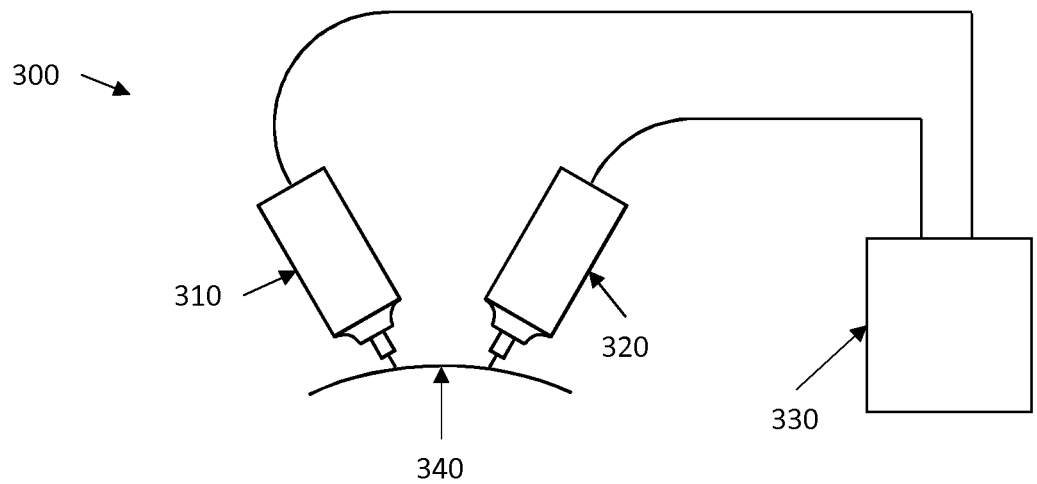
FIG. 3 is a schematic illustration of a system according to a second aspect of the present invention.

FIG. 3 shows a schematic illustration of a system 300 according to a second aspect of the present invention. The system comprising a first coaxial probe 310, a second coaxial probe 320 and a calculation unit 330. The first coaxial probe 310 is arranged to be located in connection with biological tissue 340 and to transmit a microwave signal. The second coaxial probe 320 is arranged to be located in connection with the biological tissue 340 and to receive a microwave signal. The calculation unit 330 is in connection with the first coaxial probe 310 and the second coaxial probe 320. The calculation unit 330 is being configured to calculate dielectric properties of the biological tissue based on the microwave signal transmitted and received by the coaxial probes 310, 320.

Figure 4:
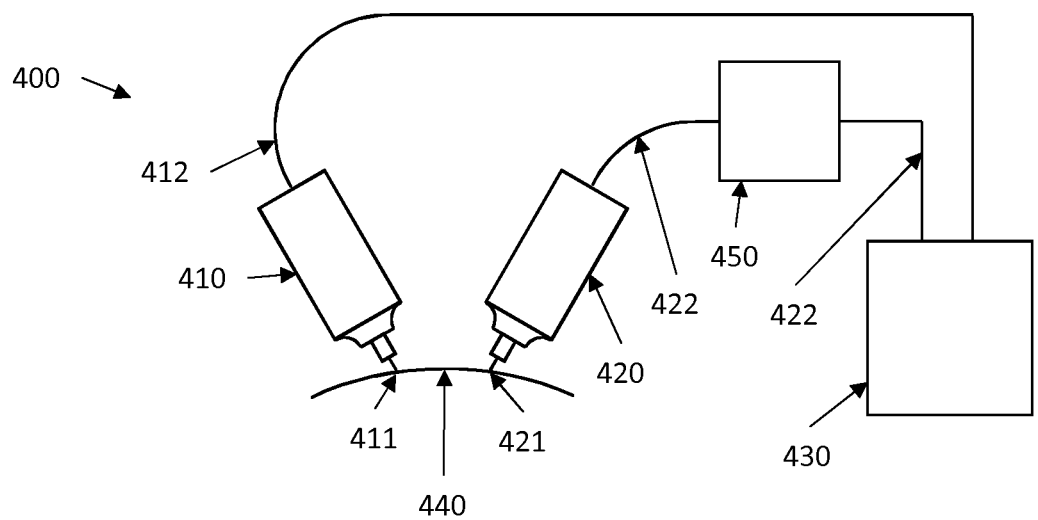
FIG. 4 is a schematic illustration of a system according to one embodiment of the invention.

FIG. 4 shows a schematic illustration of a system 400 according to one embodiment of the invention. The system comprises a first coaxial probe 410, a second coaxial probe 420, an amplification unit 450 and a calculation unit 430. The first coaxial probe 410 is arranged opposing each other and to be located in connection with bone tissue 440 and to transmit a microwave signal. The second coaxial probe 420 is arranged to be located in connection with the bone tissue 440 and to receive a microwave signal. The calculation unit 430 is in connection with the first coaxial probe 410 via a first cable 412 and the second coaxial probe 420 via a second cable 422. The amplification unit 450 is arranged on the second cable 422, the amplification unit 450 is connected to the second coaxial probe 420 and the calculation unit 430. The calculation unit 430 is being configured to calculate dielectric properties of the bone tissue 440 based on the microwave signal transmitted and received by the coaxial probes 410, 420. The end surface of the first coaxial probe 421 and the end surface of the second coaxial probe 431 are arranged to be at an angle with each other and are arranged to have an angle towards the biological tissue.

FIG. 5A shows a schematic illustration of a pincer probe 500 useful as a component in a system according to the invention. The pincer probe 500 comprises a first coaxial probe 510 mounted on a fixed arm 530 and a second coaxial probe 520 mounted on a moveable arm 540. The arms 530, 540, are mounted on a support having a scale adapted to indicate the distance "d" between the opposing ends of the coaxial probes 510, 520 as the moveable arm 540 is moved along the support 550. Other components of the system according to the invention are omitted for clarity.

FIG. 5B is an illustration of one embodiment of parts of the system according to the invention. In this embodiment specific positions, illustrated by black dots "A" and "C" on the first coaxial probe 510 and "B" and "D" on the second coaxial probe 520, are used to determine the configuration of the probes which can be used to calculate the distance d between the end surfaces of the coaxial probes 510, 520. These four points form a quadrilateral. Using geometrical relationships, it is possible to completely characterize the quadrilateral based on all four side lengths and either one interior angle or a diagonal length. Once this polygon is completely characterized it is possible to calculate the separation distance, d. The distances A to C and B to D are fixed. One way of obtaining distance measurements is to provide flexible strips having a single hole near one end which can easily slide over posts at A and C. On the other side, the strips have slots with calibrated marks along the strips. Once these are slipped over the posts at B and D, the remaining quadrilateral distances A to B (d'), C to D (d'') and A to D (d''') can easily be read off the strips. Rather than measuring the distance A to D, or C to B, it is also possible to obtain an interior angle of the quadrilateral using a protractor mounted on one of the probes. The angle between a line from an upper or lower position on one probe to the upper or lower position on the other probe (e.g. from A to B or from C to D) and a line stretching between position on the same probe (e.g. from A to C or B to D) can be determined using a protractor mounted on one of the probes. It is also possible to use other technologies for measuring distances, such as RFID.

Aspects of a general system for providing measurements of biological tissues are well known in the art and will not be described in greater detail.

EXAMPLES

Some examples illustrating and further explaining the invention are provided below. The examples are only illustrative of the invention and shall not be construed as limiting the scope of the invention, which is that defined by the appended claims.

80:20 Glycerin:Water

Figure 6:
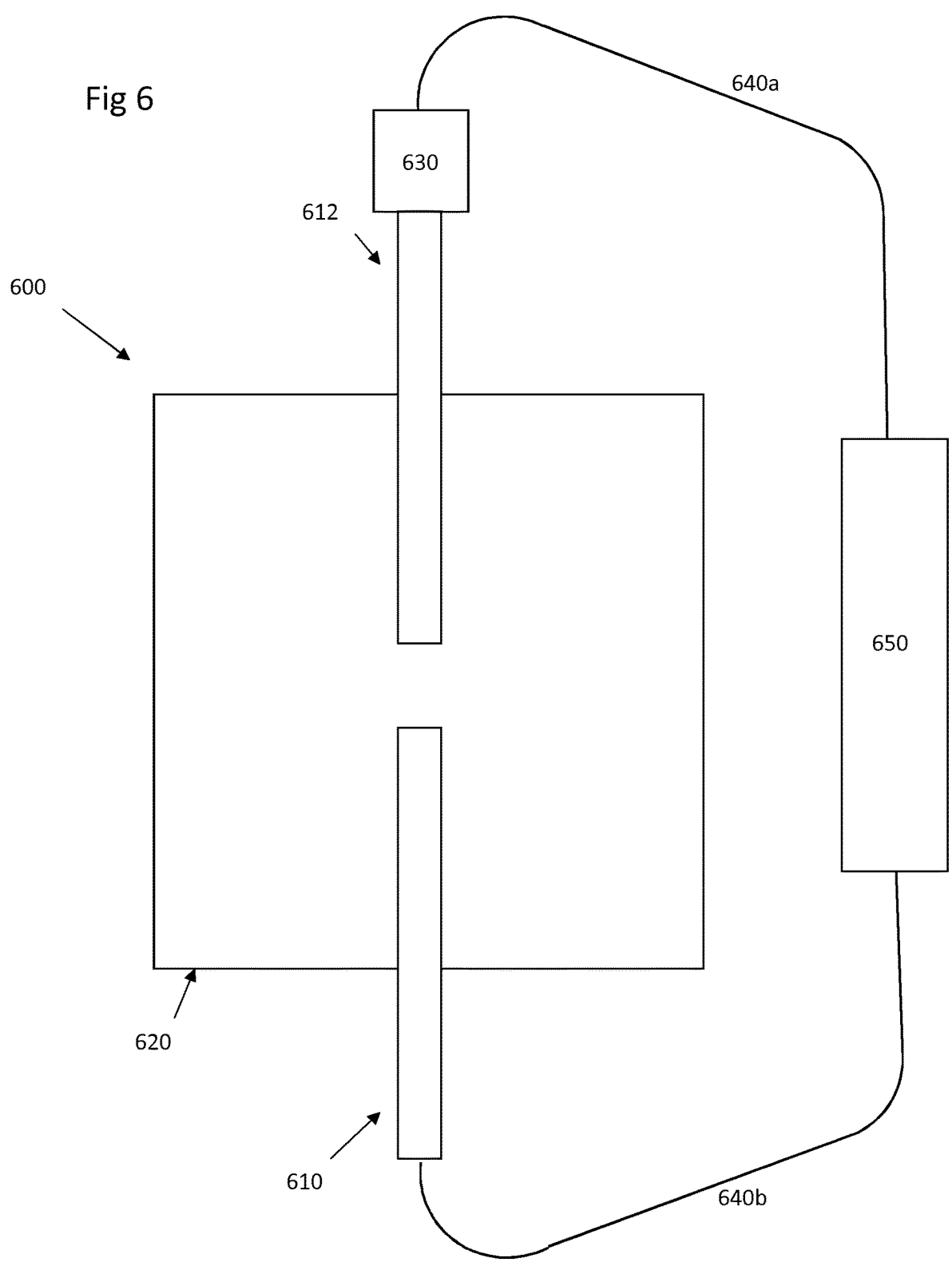
FIG. 6 is an illustration of the experimental set-up in the examples.

FIG. 6 shows a schematic diagram of the transmission probe measurement experimental set-up 600. One semi-rigid coaxial cable 610 protrudes vertically through the center of the base of a 15.2 cm diameter tank 620. A second probe 612 is attached to a micrometer 630 which is positioned at the top of the tank. Flexible coaxial cables 640a, 640b were attached to both semi-rigid coaxes and fed into the Rohde and Schwarz vector network analyzer 650 (model ZNBT8—Munich, Germany). $S_{21}$ amplitude and phase data was acquired at 201 frequencies with the IF bandwidth set to 10 Hz, along with the averaging set to a factor of 10 to maximize the dynamic range. Data was initially acquired for when the two open-ended coaxial cables were concentrically touching each other and then subsequently at 0.5 mm intervals up to a maximum separation of 4 cm. Data was acquired for three mixtures of glycerin and water because of its ability to produce a wide range of dielectric properties depending on the mixture ratios.

FIGS. 7a and b show plots of the $S_{21}$ amplitudes as a function of frequency for multiple separations for the 80:20 glycerin:water bath. The graphs are separated into a set of narrowly spaced probes spanning (a) separation distances from 0 mm to 11 mm and (b) for more broadly spaced distances from 8 mm to 20 mm. Overall the signal strengths are increasingly higher for closer separations. In addition, especially for the lower frequencies and spacings less than 4 mm, the signal strength drops off monotonically with decreasing frequency. This is a direct consequence of the opposing open-ended coaxial cables nearly approximating a series capacitor which behaves as a high pass filter. More noticeably, at frequencies below 0.5 GHz, there is a large ripple in the amplitude for separations greater than 4 mm which progressively decrease in size as the separation decreases. This is primarily caused by multi-path signals which can travel along the outer surfaces of the coaxial cables, and along the tank:liquid and tank:air interfaces [Meaney et al 2012]. In these cases, the attenuation due to propagation along these paths can be less than that for signals crossing the gap between the probes to the extent that when they recombine with the desired signals, they can add constructively and/or destructively, consequently, accounting for this rippling behavior. The phenomenon diminishes at higher frequencies because the attenuation along these alternate paths increases due to the increased liquid conductivity. This feature also diminishes for closer separations because the desired signal propagating directly across the gap is sufficiently strong to easily overwhelm the unwanted signals. These types of multi-path corruptions are typical of near field experiments and have been documented in Meaney et al [2012, 2013]. The signals at higher frequencies decrease progressively more rapidly as a function of separation distances than the lower signals. However, within the range of 2 to 6 GHz, the decrease in signal strength as a function of increasing separation is reasonably monotonic with acceptable signal strength even out to roughly 17 mm separation. This is effectively the usable bandwidth for this approach.

FIGS. 8a and b show similar plots of the $S_{21}$ amplitudes as a function of frequency for multiple separations for the 20:80 glycerin:water bath. The graphs are separated into a set of narrowly spaced probes spanning (a) separation distances from 0 mm to 11 mm and (b) for more broadly spaced distances from 8 mm to 20 mm. Overall, the signal attenuation in this liquid is lower due to the lower water content. This is evident where the attenuation for given spacings is less than that for the corresponding levels for the 80:20 glycerin bath cases. In addition, the attenuation roll-off as a function of frequency is substantially more pronounced. Interestingly, the multi-path ripples extend up to roughly 2 GHz for spacings greater than 4 mm compared to only 0.5 GHz for the 80:20 case. Even with these unwanted signals, this approach appears to remain viable from roughly 2 to 6 GHz and up to a spacing of 17 mm before becoming compromised by the noise floor.

Figure 9:
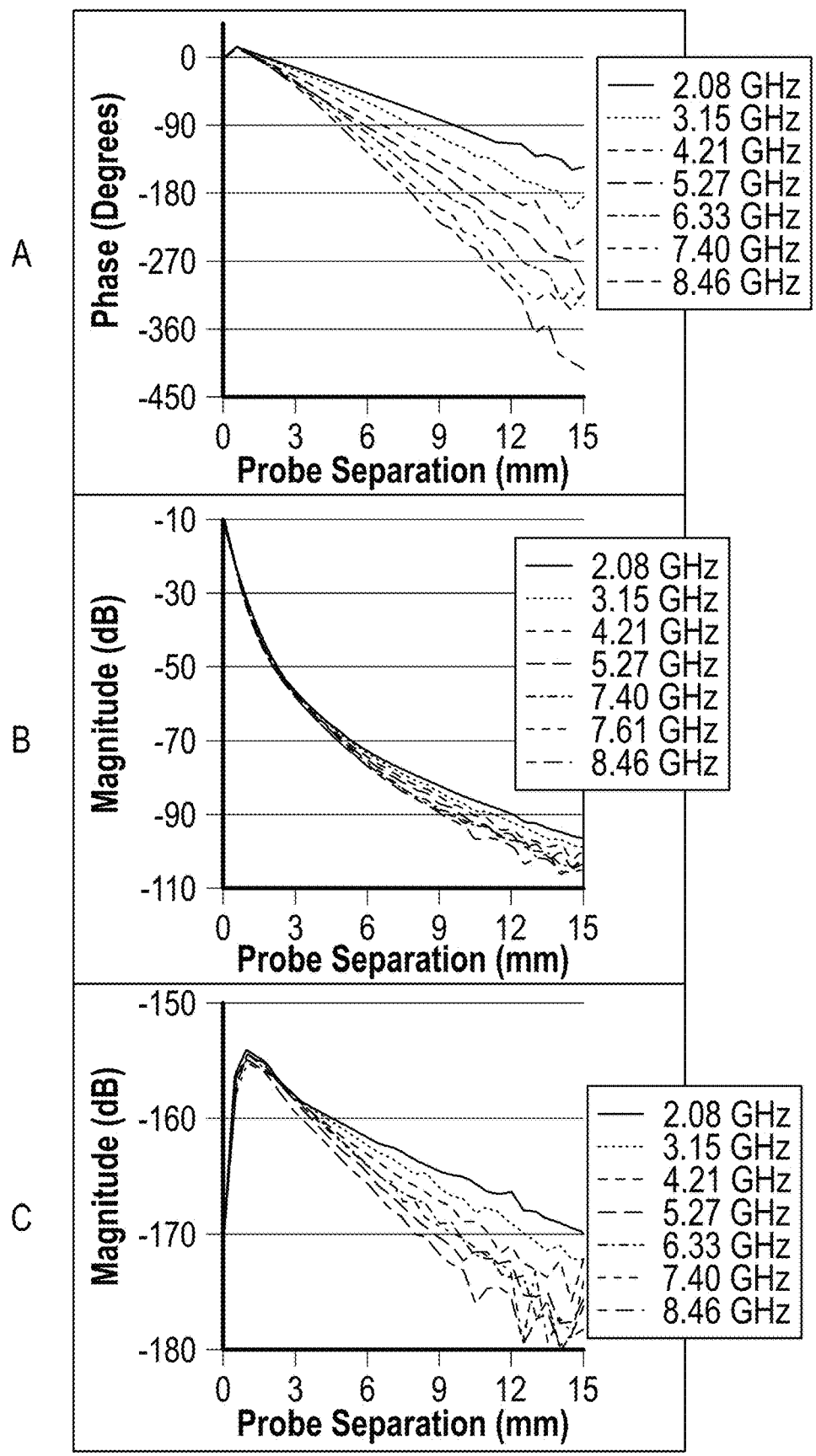
FIGS. 9A, 9B, and 9C show the phases and magnitude of the measured signals as a function of separation distance in a 80:20 glycerin:water bath.

FIGS. 9a and b show the phases and magnitude of the measured signals as a function of separation distance in the 80:20 bath for several of the frequencies within the 2 to 8.5 GHz band. The phases have all been normalized to 0 degrees when the probes are touching. As can be seen, beyond roughly a 1.5 mm separation, the phases are nearly linear with the exception of progressively increasing variability at greater distances associated with the encroaching noise floor. For analysis purposes, the slopes were determined based on least squares fits of the plots to straight lines while eliminating the data points for distances less than 1.5 mm (because of near field effects) and greater than 15 mm (because of noise corruption). For the magnitude cases, the $1/r^2$ feature is readily evident. Even with this confounding attribute, it is still clear that the attenuation per unit distance still increases with frequency. FIG. 9c shows the same data in FIG. 9b but with the $1/r^2$ term subtracted out as described above. Beyond 1.5 mm and below 15 mm, the resulting curves are roughly linear. The slopes for each were determined utilizing a least squares fit to a straight line.

Figure 10:
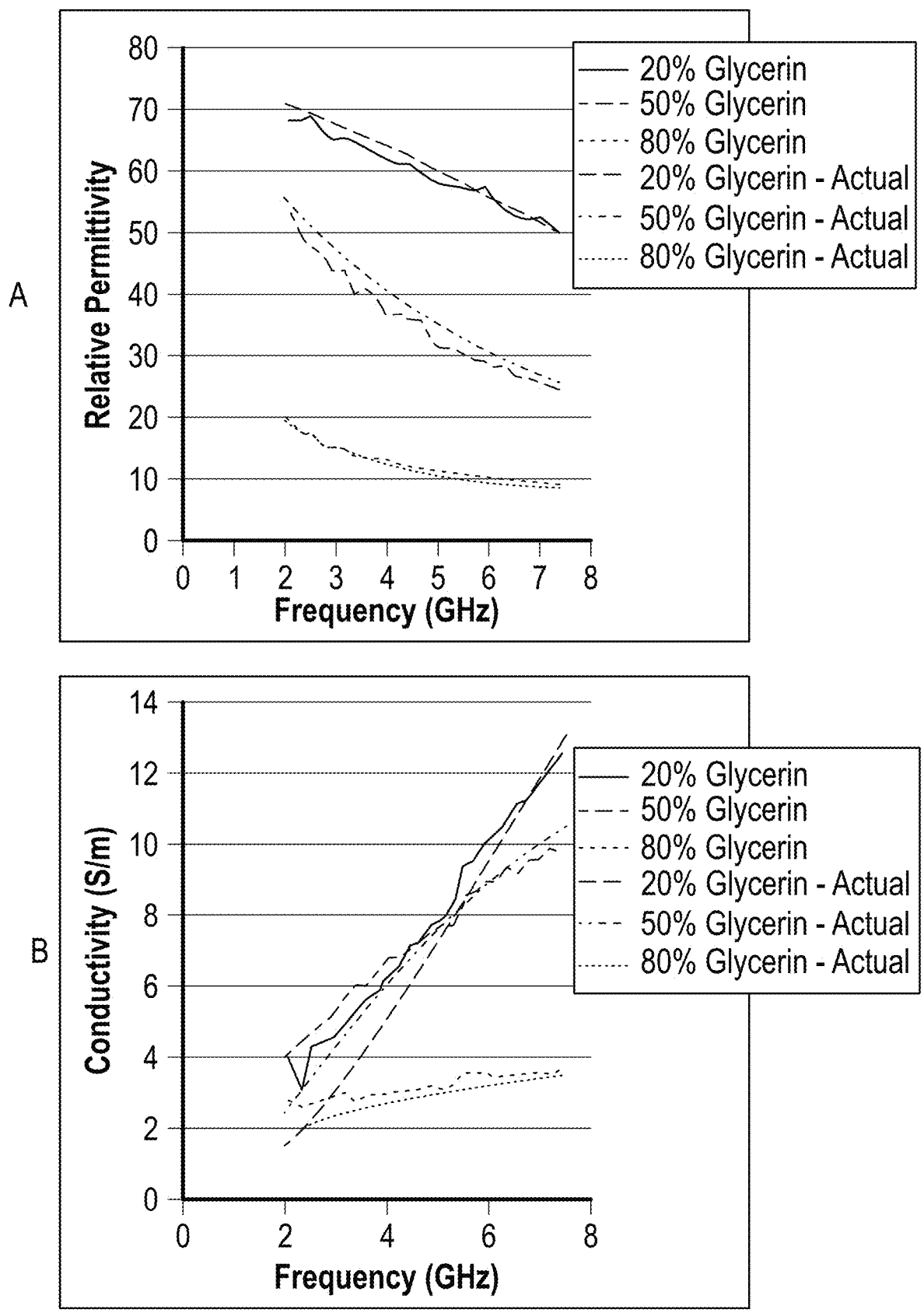
FIGS. 10A and 10B show the recovered permittivity and conductivity values, respectively, over a frequency range for three different glycerin:water mixtures (80:20, 50:50, and 20:80) utilizing the transmission-based approach according to the invention compared with ground truth measured using a standard dielectric probe kit.

FIGS. 10a and b show the recovered permittivity and conductivity values, respectively, over this frequency range for three different glycerin:water mixtures (80:20, 50:50, and 20:80) utilizing the new transmission-based approach compared with ground truth measured using the standard dielectric probe kit from Keysight Technologies. The match is quite good for both properties over the prescribed bandwidth even for the substantial range in properties for these liquids. Interestingly, it also appears that the new technique accurately mimics the characteristic dispersion curvature of the different liquids which can be quite distinct where some are concave upwards and others concave down.

This example demonstrates that utilizing two opposing open-ended coaxial probes, we can accurately recover the transmission medium dielectric properties for quite short distances. This concept is limited in applicability to testing objects where opposing sides can be accessed and the distance is short. However, the technique has important advantages over the classical, reflection-based open-ended coax probes in critical settings. For instance, the reflection based probe's penetration depth varies as a function of probe diameter and only extends roughly 280 μm for the commercial probes from Keysight Technologies. The transmission-based probes provide a more uniform assessment of the volume circumscribed by the space between the probes.

In utilizing the transmission-based probes according to the invention in a clinical setting, it will be necessary to record the magnitude and phase at two different probe separations to form slopes of the magnitude and phase as a function of separation distance. Measurements at two different separation distances are used to calculate the magnitude and phase slopes that are used to derive the dielectric properties. The first measurement will be across the tissue volume of interest. A convenient second option will include the case where the two open-ended coaxial probes directly contact each other outside of the body, or with an artificial dielectric interface (of known thickness) between them. The spacing of the probes when positioned across the volume should be determined. Various geometrical triangulation techniques may be used for estimating the spacing of the probes when positioned across the tissue volume, or otherwise at a distance from each other.

Tissues

The present invention may be used in relation to any biological tissue and is useful in assessing their physiological properties. This in turn finds use in both clinical practice as well as in research. Some examples where the invention may be put to use are provided below. These are however only illustrative of the invention and shall not be construed as limiting the scope of the invention, which is that defined by the appended claims.

Bone Tissue

One example is in the area of bone density measurements in orthopaedic procedures wherein a fastening element is to be fastened in bone tissue. It is then desirable to assess the physiological properties, such as density and/or strength, of the bone tissue in order to use the most suitable fastening element for the patient. The fastening element may be a part of a prosthesis to be fastened in a bone, such as a hip prosthesis to be fastened in a femur or a tooth prosthesis to be fastened in a jaw bone, or an element used to fixate parts of a fractured bone or fixate two bones in relation to each other.

One such example is in the area of bone density measurements of vertebrae during spinal fusion surgeries. Back pain and injuries are significant health problems in North America and northern European countries. In these cases, the spinal column needs to be held immobile for a lengthy period of time until adjoining vertebrae become substantially fused. For these situations, instrumentation is installed over a length of multiple vertebrae to hold the column in place. A very common type of instrumentation involves posterior pedicle screws connected by rods in several continuous vertebrae to supply sufficient support. It is critical that the vertebrae are strong enough to withstand the forces exerted through the screws. The overall surgical success rate is decreased in bone with low density. Instrumentation failure or loosening can lead to significant patient pain and inconvenience, trauma and high costs of repeated surgeries. Using the invention to provide direct measures of the bone tissue during surgery may assist in the decision making and thereby minimize the number of repeated surgeries, reducing health care costs while improving overall patient quality of life. In cases where the dielectric probe results indicate that the vertebrae are weak, alternative surgical strategies can be used to improve the probability of success.

In cases where the bones are insufficiently strong, there are alternatives. For instance, augmenting with bio-compatible cements can be used to strengthen the bone:screw interface. This has been used widely, but there is a small risk of a piece of cement breaking off and entering the blood stream and eventually causing an embolism and the effect on load sharing might further be negative. Other approaches include using specially designed screws or involving more vertebrae to reduce the physical load on each screw. This obviously requires a more invasive surgery with concomitant health risks.

The method and system according to the invention provide a more definitive measure of vertebrae suitability on a bone by bone basis directly during the surgical session, allowing the surgical team to create an individually designed surgery plan and performance.

Historically, dielectric probe measurements of bone have been challenging because of the different issues discussed above. These are further complicated by the fact that the measurements would need to be performed in vivo. This setting could prove particularly intriguing because the clinician has access to the vertebrae from two sides through the opposing pedicle canals. While the orientation of a pair of standard open-ended coaxial cables would not be aligned perfectly, in a more refined implementation, simple, custom bends in the coaxial probes can be added to provide the desired configuration.

Skin Tissue

The method and system according to the present invention may be used on skin tissue to assess presence, absence, or malignancy of various conditions.

Leishmaniasis is a complex of vector-borne diseases caused by protozoan parasites of the genus Leishmania transmitted by the bite of phlebotomine sandflies. A dozen nosogeographical entities—characterized by different parasite, vector and reservoir host species, geographical distribution and clinical features in humans—affect 101 countries in tropical, subtropical and temperate zones of the world. More than 90% of 200,000-400,000 global cases of visceral leishmaniasis (VL), the most severe form, are estimated to occur annually in endemic areas of India, Bangladesh, Sudan, South Sudan, Ethiopia and Brazil. Post-kala-azar dermal leishmaniasis (PKDL) is a complication of visceral leishmaniasis (VL). In Leishmania endemic areas, the clinical manifestation of Post Kala Azar Dermal Leishmaniasis (PKDL) can mimic other dermatological lesions, which makes the diagnosis of this condition more difficult. To date there are no accurate or precise ways to diagnose PKDL patient and most of the methods used possess low sensitivities. As a result most true positives are missed; these positive PKDL patients with a negative misdiagnosis will act as a reservoir for VL transmission and hence failure for VL elimination. Additionally, low sensitivities generate false positives resulting in unnecessary treatment for negative PKDL patients with associated waste and avoidable exposure to toxic drugs. To date there are no specific tests or techniques with high sensitivity and specificity that can discriminate between PKDL patients and other dermatological lesions.

The present invention provides a robust, completely non-invasive, coaxial waveguide based transmission mode analysis for improved PKDL detection accuracy.

Figure 5:
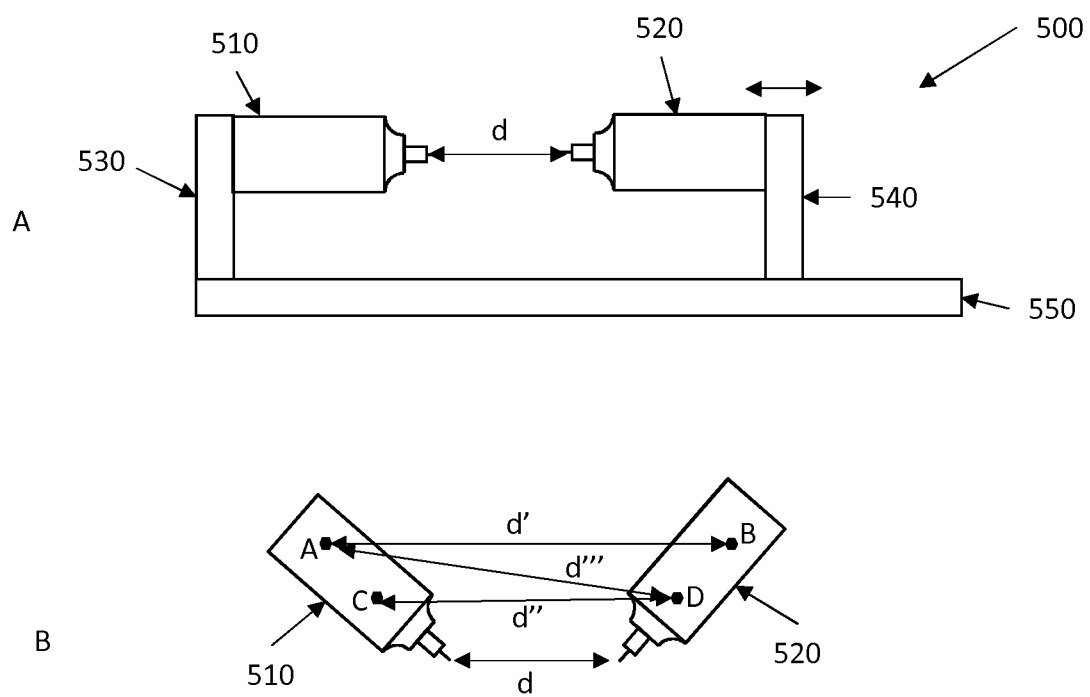
FIGS. 5A and 5B are schematic illustrations of parts of a system according to the invention.

The system according to the invention can be designed for non-invasive monitoring of skin lesions, such as those manifested by Leishmaniasis. A conceptual image of the system is shown in FIG. 5. The sensors are envisioned in the shape of small pincers facilitating in-face alignment of transmitted and received signal across (through) the dermatological lesions. The pincers are provided with calipers to measure the thickness of the lesion which will in turn help in the calibration. These sensors are expected to perform data acquisition in microseconds and thus discomfort will be minimal. The signal may be generated by a 2 port copper mountain computer driven vector network analyzer (VNA). The VNA will also be able to receive the signal and send it to a computer with post processing software. Since the dermatological lesions carry granulomatous (inflammatory) formations typical to leishmaniasis, it will be very important to find patterns in the received signal that have traversed through the target. Advanced signal analysis techniques such as machine learning may be employed in the post processing software for improving the detection accuracy. The theory behind this is that the variation in dielectric constant at the target site compared to healthy skin samples is due to physiological differences. The dielectric variation plays a role in the absorption and affects the transmission of the signal through the lesion.

Other applications on skin tissue are detection, or assessment of malignancy, of skin cancer lesions, such as melanoma.

While specific embodiments have been described, the skilled person will understand that various modifications and alterations are conceivable within the scope as defined in the appended claims.

The invention claimed is:

1. A method for assessing at least one physiological property of a biological tissue, the method comprising the steps of:
   transmitting a microwave signal from a first coaxial probe having a first end surface positioned 5 mm or less from the biological tissue;
   receiving the microwave signal at a second coaxial probe having a second end surface positioned 5 mm or less from the biological tissue, wherein the first end surface is arranged at a distance of 1.5 mm to 5 cm from the second end surface; and
   assessing the at least one physiological property of the biological tissue based on (a) the distance and (b) far field measures of the microwave signal transmitted and received across the biological tissue between the coaxial probes.

2. The method according to claim 1, wherein the assessment of the at least one physiological property of the biological tissue is based on the far field measures having amplitudes and linearly varying phases of the microwave signal transmitted and received across the biological tissue between the coaxial probes.

3. The method according to claim 2, wherein the assessment of the at least one physiological property is based on a calculation of a dielectric property of the biological tissue based on the microwave signal.

4. The method according to any claim 3, wherein the dielectric property is selected from the group consisting of dielectric constant, relative permittivity, and conductivity.

5. The method according to claim 1, wherein the first coaxial probe and the second coaxial probe are arranged on opposite sides of the biological tissue and the first end surface and the second end surface are arranged to be parallel, or at an angle of less than 90°, and opposing each other.

6. The method according to claim 1, wherein the first coaxial probe and the second coaxial probe are arranged on the same side of the biological tissue and the first and second end surfaces are arranged to be parallel, or at an angle of no more than 90°.

7. The method according claim 1, wherein the biological tissue is bone tissue.

8. The method according to claim 7, wherein the first coaxial probe is inserted in a first pedicle canal in a vertebrae and a second coaxial probe is inserted in a second pedicle canal in the vertebrae.

9. The method according to claim 7, wherein the assessment of the physiological property is based on a calculation of a dielectric property, correlated to bone density, of the bone tissue.

10. The method according to claim 1, wherein the microwave signal is transmitted using a software defined radio.

11. The method according to claim 1, wherein the microwave signal has a frequency greater than 2 GHz and less than 8.5 GHz.

12. The method according to claim 1, wherein the biological tissue is bone tissue and the physiological property is selected from the group consisting of: bone density and bone strength.

13. The method according to claim 1, wherein the first coaxial probe and the second coaxial probe are arranged on a same side of the biological tissue and the first end surface and the second end surface are arranged to be parallel, or at an angle of less than 90°, and adjacent one another.

14. The method of claim 1, wherein the biological tissue comprises one or more of: skin tissue, connective tissue, tendons, cartilage, muscle, adipose tissue, fibrous tissue, or organ tissue.

15. A system for assessing at least one physiological property of a biological tissue, the system comprising:
- a first coaxial probe for transmitting a microwave signal and having a first end surface arranged 5 mm or less from the biological tissue;
- a second coaxial probe for receiving the microwave signal and having a second end surface arranged 5 mm or less from the biological tissue, the-first end surface being separated from the second end surface by 1.5 mm to 5 cm;
- a calculation unit in connection with the first coaxial probe and the second coaxial probe, the calculation unit being configured to:
- calculate an assessment of the at least one physiological property of the biological tissue based on (a) the distance and (b) the far field microwave signal transmitted and received across the biological tissue between the coaxial probes.

16. The system according to claim 15, wherein the first end surface and the second end surface are arranged to be opposing each other and parallel, or at an angle of less than 90°, with each other.

17. The system according to claim 16, wherein the first coaxial probe and the second coaxial probe are arranged on a pincer or caliper.

18. The system according to claim 15, wherein the first end surface and the second end surface are arranged to be parallel and arranged side-by-side.

19. The system according to claim 15, wherein the calculation unit is configured to calculate at least one dielectric property of the biological tissue based on the microwave signal transmitted and received across the biological tissue between the coaxial probes and to calculate an assessment of the at least one physiological property of the biological tissue based on said calculated dielectric property.

* * * * *